(12) United States Patent
Krastev

(10) Patent No.: US 10,631,958 B2
(45) Date of Patent: Apr. 28, 2020

(54) VARIABLE GEOMETRY OSTEOTOME SET WITH MULTIPLE MODES OF USE FOR IMPLANT SOCKET FORMATION

(71) Applicant: Pavel Krastev, New Hyde Park, NY (US)

(72) Inventor: Pavel Krastev, New Hyde Park, NY (US)

(*) Notice: Subject to any disclaimer, the term of this patent is extended or adjusted under 35 U.S.C. 154(b) by 108 days.

(21) Appl. No.: 15/936,879

(22) Filed: Mar. 27, 2018

(65) Prior Publication Data

US 2018/0289453 A1 Oct. 11, 2018

Related U.S. Application Data

(63) Continuation-in-part of application No. 15/936,693, filed on Mar. 27, 2018.

(Continued)

(51) Int. Cl.
*A61C 8/00* (2006.01)
*A61B 17/16* (2006.01)
(Continued)

(52) U.S. Cl.
CPC ........ *A61C 8/0089* (2013.01); *A61B 17/1604* (2013.01); *A61B 17/1673* (2013.01); *A61C 1/10* (2013.01); *A61C 1/12* (2013.01); *A61C 8/0092* (2013.01); *A61B 90/94* (2016.02); *A61B 2090/062* (2016.02); *A61C 2201/002* (2013.01)

(58) Field of Classification Search
CPC ....... A61C 8/00; A61C 8/0089; A61C 8/0092; A61C 1/10; A61C 1/12; A61B 17/16; A61B 17/1673; A61B 90/04
See application file for complete search history.

(56) References Cited

U.S. PATENT DOCUMENTS 1,279,495 A 9/1918 Dom
2,984,241 A 5/1961 Carlson
(Continued)

OTHER PUBLICATIONS

Summers, Robert B, DMD, "A New Concept in Maxillary Implant Surgery: The Osteotome Technique"; Compend. Contin. Educ. Dent., vol. XV, No. 2; 1994; 6 pages.
(Continued)

*Primary Examiner* — Christopher J Beccia
(74) *Attorney, Agent, or Firm* — Thomas A. O'Rourke; Bodner & O'Rourke, LLP

(57) ABSTRACT

A set of osteotomes have conical tips with free end diameters alternately increasing by a constant increment, k, as a step function, beginning with the first osteotome; and working base diameters alternately increases by a constant increment, C, as a step function, beginning with the second osteotome. For seven osteotomes, the first and second diameters respectively are: 1 mm and 2 mm; 1 mm and 3 mm; 2 mm and 3 mm; 2 mm and 4 mm; 3 mm and 4 mm; 3 mm and 5 mm; and 4 mm and 5 mm. In a first mode all seven osteotomes are used to provide very gradual diameter escalations. In a second mode the first, third, fifth, and seventh osteotomes provide conventional Summers' diameter escalations. In third and fourth modes the first, fourth, and seventh osteotomes, and the second, fifth, and seventh osteotomes respectively provide increasingly more aggressive Summers' type escalations.

20 Claims, 13 Drawing Sheets

Related U.S. Application Data

(60) Provisional application No. 62/482,727, filed on Apr. 7, 2017, provisional application No. 62/482,748, filed on Apr. 7, 2017.

(51) Int. Cl.
*A61C 1/10* (2006.01)
*A61C 1/12* (2006.01)
*A61B 90/94* (2016.01)
*A61B 90/00* (2016.01)

(56) References Cited

U.S. PATENT DOCUMENTS

| | | | |
|---|---|---|---|
| 3,678,934 | A | 7/1972 | Warfield |
| 3,986,512 | A | 10/1976 | Walliser |
| 4,112,944 | A | 9/1978 | Williams |
| 4,150,675 | A | 4/1979 | Comparetto |
| 4,412,825 | A | 11/1983 | Tokarz |
| 4,600,005 | A | 7/1986 | Hendel |
| 4,673,353 | A | 6/1987 | Nevin |
| 4,881,534 | A | 11/1989 | Uhl |
| 5,049,125 | A | 9/1991 | Accaries |
| D324,424 | S | 3/1992 | Michelson |
| 5,188,488 | A | 2/1993 | Nakayama |
| D338,528 | S | 8/1993 | Koros |
| D342,313 | S | 12/1993 | Hood |
| 5,291,914 | A | 3/1994 | Bares |
| 5,312,255 | A | 5/1994 | Bauer |
| 5,584,688 | A | 12/1996 | Sakuma |
| 5,722,977 | A | 3/1998 | Wilhelmy |
| 5,915,967 | A | 6/1999 | Clokie |
| 5,997,298 | A * | 12/1999 | Nowak ............... A61B 17/1604 433/165 |
| 6,171,312 | B1 | 1/2001 | Beaty |
| 6,200,289 | B1 | 3/2001 | Hochman |
| D450,844 | S | 11/2001 | Lewis |
| 6,485,495 | B1 | 11/2002 | Jenkinson |
| 6,537,280 | B2 | 3/2003 | Dinger |
| 6,790,211 | B1 | 9/2004 | McPherson |
| 6,899,715 | B1 | 5/2005 | Beaty |
| 7,100,476 | B1 | 9/2006 | Feit |
| 7,125,253 | B2 | 10/2006 | Kitamura |
| 7,217,130 | B2 | 5/2007 | Giorno |
| 7,241,144 | B2 * | 7/2007 | Nilo ..................... A61C 8/0089 433/141 |
| 7,396,232 | B2 | 7/2008 | Fromovich |
| 7,547,210 | B1 | 6/2009 | Valen |
| 7,632,280 | B2 | 12/2009 | Hochman |
| 7,771,199 | B2 | 8/2010 | Hochman |
| 8,029,284 | B2 | 10/2011 | Better |
| 8,083,747 | B2 | 12/2011 | Song |
| D653,339 | S | 1/2012 | Ross |
| 8,282,640 | B2 | 10/2012 | Hung |
| 8,480,675 | B2 | 7/2013 | Betts |
| 9,011,446 | B1 | 4/2015 | Henderson |
| 9,028,253 | B2 | 5/2015 | Huwais |
| 9,198,743 | B2 | 12/2015 | Wang |
| 9,498,308 | B1 | 1/2016 | Krastev |
| 9,289,218 | B2 | 3/2016 | Courtney |
| 9,326,778 | B2 | 3/2016 | Huwais |
| 9,333,058 | B1 * | 5/2016 | Krastev ............... A61C 8/0089 |
| 9,421,028 | B2 | 8/2016 | Darian |
| 9,526,593 | B2 | 12/2016 | Huwais |
| 9,603,720 | B2 | 3/2017 | Kelley |
| 2002/0094508 | A1 | 7/2002 | Lorenzi |
| 2003/0228556 | A1 | 12/2003 | Giorno |
| 2006/0020326 | A9 | 1/2006 | Bokluc |
| 2006/0172255 | A1 | 8/2006 | Hochman |
| 2006/0271056 | A1 | 11/2006 | Terrill-Grisoni |
| 2007/0042326 | A1 | 2/2007 | Cardoso |
| 2007/0055257 | A1 | 3/2007 | Vaccaro |
| 2007/0293871 | A1 | 12/2007 | Ackerman |
| 2008/0188878 | A1 | 8/2008 | Young |
| 2008/0215010 | A1 | 9/2008 | Silver |
| 2008/0275379 | A1 | 11/2008 | Kurrek |
| 2008/0319466 | A1 | 12/2008 | Eder |
| 2009/0042158 | A1 | 2/2009 | Steiner |
| 2009/0274996 | A1 | 11/2009 | Miller |
| 2009/0292288 | A1 | 11/2009 | Hung |
| 2009/0326440 | A1 | 12/2009 | Lee |
| 2010/0196841 | A1 | 8/2010 | Nahlieli |
| 2010/0221681 | A1 | 9/2010 | Hochman |
| 2010/0291511 | A1 | 11/2010 | Lee |
| 2010/0324561 | A1 | 12/2010 | Watzek |

OTHER PUBLICATIONS

Summers, Robert B, DMD, "The Osteotome Technique: Part 2—The Ridge Expansion Osteotomy (REO) Procedure"; Compend. Contin. Educ. Dent., vol. XV, No. 24 1994; 7 pages.

Vladimir Koifman, "Fraunhofer Institute and Awaiba Developed 1 mm>3 Camera," Image Sensors World, News and Discussions about Image Sensors, Mar. 11, 2011.

Muronoi M, er al., "Simplified procedure for augmentation of the sinus floor using a haemostatic nasal balloon," British J of Oral & Maxillofacial Surgery 41(2):120-121, 2003.

Hernandez-Alfaro F, sr al., Prevalence and management of Schneiderian membrane perforations during sinus-lift procedures. Clin. Oral Impl. Res. 19, 2008; 91-98.

Javier Ferrer, et. al., "Analysis of the Use of Expansion Osteotomes for the Creation of Implant Beds . . . echnical Contributions and and Review of the Literature," 2006.

Laksman Dene; Ridge Expansion and Immediate Implant Placement in the Esthetic Zone; NYSDY; Mar. 2010; 4 pages.

* cited by examiner (Set of Straight Osteotomes)
MODE 1 - Tools: 0, 1, 2, 3, 4, 5, and 6
Alternating Stepped Escalation MODE 2 - Use only Tools: 0, 2, 4, and 6 of FIG. 1
(Traditional Summers Escalation)

MODE 3 - Use only Tools: 0, 3, and 6 of FIG. 1 (Aggressive Summers-type Escalation)

MODE 4- Use only Tools: 1, 4, and 6 of FIG. 1
(More Aggressive Summers-type Escalation)

(Set of Angular Osteotomes)
MODE 1 - Tools: 1, 2, 3, 4, 5, and 6
Alternating Stepped Escalation MODE 2 - Use only Tools: 1, 4, and 6 of FIG. 5
Summers Type Escalation MODE 3 - Use only Tools: 2, 4, and 6 of FIG. 5
Aggressive Summers Type Escalation MODE 4- Use only Tools: 1 and 5 of FIG. 5
More Aggressive Summers Type Escalation

MODE 2 - Use only Tools: 1, 4, and 6 of FIG. 9
Summers Type Escalation

MODE 3- Use only Tools: 1 and 5 of FIG. 9
Aggressive Summers Type Escalation

MODE 4- Use only Tools: 2, 4, and 6 of FIG. 9
Aggressive Summers Type Escalation

VARIABLE GEOMETRY OSTEOTOME SET WITH MULTIPLE MODES OF USE FOR IMPLANT SOCKET FORMATION

CROSS REFERENCES TO RELATED APPLICATIONS

This application is a continuation in part of U.S. patent application Ser. No. 15/936,693, filed on Mar. 27, 2018, titled "Osteotome set for Dental Implant Socket Formation with Alternating Base and Crestal Work Areas," and this application also claims priority on U.S. Provisional Application Ser. No. 62/482,727, filed on Apr. 7, 2017, titled "VGO Drill Concept," all disclosures of which are incorporated herein by reference.

FIELD OF THE INVENTION

The subject technology relates generally to improvements in osteotomes and equipment for enhancing the use of osteotomes that can be used in a variety of procedures, including, but not limited to ridge expansion, bone densification, ridge splitting, crestal sinus elevation, etc.

BACKGROUND OF THE INVENTION

There are many conditions which may result in a person becoming partially or completely edentulous (periodontal disease, an injury, etc.), which is commonly remedied today by dental implants. Dental implants are endosseous, being a "root" device that is usually made of titanium, where the implants are inserted into the jaw through the bone at the alveolar ridges, after which a healing period on the order of months is necessary for osseointegration. During this healing period the bone will grow in and around the implant to provide support.

The alveolar ridges are columns of bone, found on both the maxilla and the mandible, that surround and anchor the teeth within sockets known as alveoli. However, the alveolar bone quickly becomes atrophic in the absence of teeth, typically resulting in lack of sufficient bone mass for successful implantation. In the Maxilla, when sinus pneumatization decreases available bone after tooth loss, a sinus elevation procedure prior to implant placement is required to increase the amount of bone therein. The sinus lift procedure may be performed either through a lateral approach or a crestal approach.

In the crestal approach for a sinus lift procedure of the posterior maxilla (upper jaw), to which the improvements of the present invention is directed, a pilot drill may initially be used to create a small hole in the crestal cortex to reach the cancellous layer, and to form an implant insertion axis. The anatomical characteristics of the posterior maxilla, particularly the existence of its more spongy (cancellous) bone, enable it to successfully lend itself to undergo the ridge expansion osteotomy technique developed by R. B. Summers (see e.g., Summers, D M D, Robert B. "A New Concept in Maxillary Implant Surgery: The Osteotome Technique;" 1994; Summers, D M D, Robert B. "The Osteotome Technique: Part 2—The Ridge Expansion Osteotomy (REO) Procedure;" 1994; and Summers, D M D, Robert B. "The Osteotome Technique: Part 3-Less Invasive Methods of Elevating the Sinus Floor;" 1994).

The technique causes expansion of the pilot hole without further elimination of bone material, and generally tends to compresses the bone and increases bone density, in the surgeon's favor. The technique uses a succession of conical expansion Osteotome tools having a gradual diameter escalation. The smallest caliber expansion Osteotome tool is inserted manually into the pilot hole, with pressing and rotating of the tool occurring until the desired depth is reached, or until further penetration is resisted, at which time gentle tapping using a surgical mallet on the Osteotome may cause it to reach the proper depth. Further use of successively larger Osteotome tools causes lateral compression that increases bone density and the size of the opening. The procedure is typically carried out by an oral surgeon using different calibers of Osteotomes that are constructed in accordance with the Summers' diameter escalation scheme, whereby the initial diameter of a successively larger Osteotome is the same as the largest penetrating diameter of the previous conical Osteotome that was used, thereby providing a constant progression of increasing separation.

The procedure exhibits high success rates if the sinus membrane was not breached during the procedure, as discussed in the article by Hernandez-Alfaro F, Torradeflot M M, and Marti C., titled "Prevalence and Management of Schneiderian Membrane Perforations during Sinus-lift Procedures." But a further consideration for the success of the implant concerns the impact of the Summers' diameter escalation on the crest of the alveolar ridge, when the ridge has undergone resorption producing a knife-edged shape, rather than its tall, rounded shape.

The present invention offers various improvements to aid the oral surgeon, including a particularly formed set of Osteotomes, all of which or only some of which may be utilized in various different modes of use, one of which may be particularly selected for an individual patient for implant socket formation to reduce fracturing proximate to the base or proximate to the crest of the alveolar ridges during the osteotomy.

OBJECTS OF THE INVENTION

It is an object of the invention to provide a set of Osteotomes that are particularly constructed to perform a ridge expansion osteotomy.

It is another object of the invention to provide a series of ridge expansion Osteotomes that are particularly adapted to reduce stress on the crestal cortex to reduce the possibility of fracture.

It is a further object of the invention to provide a set of Osteotomes that are particularly adapted for each osteotome of the set to be used to accomplish implant socket formation in a safer, more gradual approach to prevent fracture of the crestal cortex.

It is also an object of the invention to provide a set of osteotomes that are labeled, so that all or some of the osteotomes of the set may be quickly identified and used for a particular patient in one of several different modes of use.

It is another object of the invention to provide a set of osteotomes that are particularly marked to identify to the dental implant surgeon which part of the tip is active.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

To the untrained eye all osteotomes on the market look similar to each other. Generally, osteotomes can be either the straight type, or of the offset type, also known in the art as the angulated type. These instruments may be designed to be multi purposeful. They can be used for bone spreading and densitication, for ridge expansion, ridge splitting, and very often for the crestal sinus elevation procedure. The straight type tools are predominantly used in the anterior or front portion of the mouth. The offset type tools are predominantly used in the posterior or back portion of the mouth to facilitate reaching back into the small space. Due to the nature of such design and use, it may be understood that rotational hand motion is generally easier to accomplish with the straight type osteotomes than with the angulated type. The offset type osteotomes have an angular component in their design, which, when used in the back of the mouth, makes pure rotational motion difficult to accomplish. For this and other reasons, a mallet is typically used for implant socket formation using the offset type of osteotomes. The straight type osteotome being used in the anterior of the mouth, can be manipulated with pure hand rotation, or with the use of a mallet.

A thread may be incorporated on the working portion of the conical tip of the osteotome, and when used in softer bone, hand force may be sufficient for socket formation, but in denser bone, a mallet is often required. However, use of a mallet and the associated banging often causes an undesired side effect in the patient known as vertigo. Vertigo is a disturbance of the inner ear apparatus that is involved in balance, control, and coordination. A patient that may be susceptible to vertigo can experience dizziness, and a diminished capacity to conduct with one's daily activities. When vertigo is caused by use of osteotomes, particularly the malleting of the osteotome, it will usually be self-limiting. For this reason, use of a mallet should be minimized, and the formation of the socket should be accomplished with as little disturbance to the patient as possible, while preserving bone mass.

In the past, many if not most dental implant surgeons utilized a set of osteotomes, each having a conical tip, the apex and base diameters of which increased according to the above-mentioned formula devised by R. B. Summers. With the Summers' formulation, the initial diameter of a successively larger osteotome is the same as the largest penetrating diameter of the previous osteotome used, thereby providing a constant progression of increasing separation.

However, there are some problems with traditional Summers' type osteotomes, and their associated tapers. The Summers' diameter escalation scheme essentially serves to apply a constant linear dilation to the bony osteotomy (i.e., the implant socket), beginning at the crest for each successive osteotome. But, as dental implant surgeons are all aware, the residual bony ridge is typically thin at the crest, and widens in the apical direction. i.e., the bone ridge becomes wider and wider in the apical direction, and is therefore less conducive to flexing. Therefore, typical Summers' type osteotomes simply apply this linear force too aggressively onto the thin crestal portion of the residual ridge. This excessive initial force applied to the thin, vulnerable crestal bony portion often leads to its fracture. Most osteotomes attempt to hinge the bony walls too fast and too close to the crest without any consideration to making the deeper bone more conducive to flexing prior to trying to dilate the thin crest.

The variable geometry osteotome (VGO) sets disclosed herein address these problems, and thereby makes the entire process of expanding thin ridges much safer. The VGO sets disclosed herein further provide flexibility of use that no other osteotome kits on the market offer, namely being four different modes of use. This gives the surgeon more options to have as they may be needed depending on different bone densities encountered for different patients.

The VGO sets use a dual stepwise escalation for the diameters of both tip apices and tip bases, instead of the Summers' linear escalation of most osteotome sets on the market. This dual stepwise escalation of the complete set provides for passive entrance at the thin and vulnerable Crestal portion of hole, and thus produces little or no stress on the thin crestal bone, as each successive tip engages the deeper, wider, and stronger bone. The VGO tips work in succession, where each osteotome tip first prepares the bony hole for what the next osteotome tip will do. The VGO tips work on the deeper bony portion first and thereby moves the hinge axis into deeper bone, prior to attempting to spread the thinner, weaker crestal bone. By doing work deeper inside the implant socket first, the bony walls are made thinner and are therefore more conducive to be able to flex when the next tool is introduced into hole. This imposes less stress on the thin crest, and makes the expansion process much safer and more predictable.

In one embodiment, each straight-type osteotome of the set may have a conical working tip with a free end having a diameter $\phi_{An}$, and a working base having a diameter $\phi_{Bn}$. The first osteotome, n=1, of the set may have the working tip formed with a first diameter, $\phi_{A1}$ at the free end, and a second diameter, $\phi_{B1}$ at the working base, where the second diameter is larger than the first diameter, $\phi_{Bn} > \phi_{An}$ for each osteotome of the set to provide the conical shape. The diameter at the free end alternately increases by a constant increment, k, as a step function, for each successive osteotome of the set beginning with the first osteotome; and the diameter at the working base alternately increases by a constant increment, C, as a step function, beginning with a second osteotome of the set. For a set of seven osteotomes in this embodiment, the dual stepped diameter escalation may be as shown in the following chart:

| Osteotome Tool Number | Diameter Tip Apex (mm) | Diameter Tip Base (mm) |
| --- | --- | --- |
| 0 | 1 | 2 |
| 1 | 1 | 3 |
| 2 | 2 | 3 |
| 3 | 2 | 4 |
| 4 | 3 | 4 |
| 5 | 3 | 5 |
| 6 | 4 | 5 |

In a first mode of use, each of the seven osteotomes are successively worked into the implant socket for a very gradual escalation. In a second mode of use, only the first osteotome (Tool "0"), the third osteotome (Tool "2"), the fifth osteotome (Tool "4"), and the seventh osteotome (Tool "6") are successively worked into the implant socket for a typical Summers diameter escalation. In a third mode of use, only the first osteotome (Tool "0"), the fourth osteotome (Tool "3"), and the seventh osteotome (Tool "6") are successively worked into the implant socket for a more aggressive Summers diameter escalation—being more aggressive in that the escalation to the highest diameter occurs using fewer steps/osteotomes. In a fourth mode of use, only the second osteotome (Tool "1"), the fifth osteotome (Tool "4"), and the seventh osteotome (Tool "6") are successively worked into the implant socket for an even more aggressive Summers' diameter escalation—being more aggressive in that the escalation to the highest diameter occurs using larger diameters.

Each of the osteotomes may include a first marking that may be the number "1," to indicate usage of each of the seven osteotomes in the first mode of use in implant socket formation. Each of the first, the third, the fifth, and the seventh osteotomes may also have a second marking thereon that may be the number "2," to indicate usage of only the first, third, fifth, and seventh osteotomes in the second mode of use in implant socket formation. Each of the first, the fourth, and the seventh osteotomes may also have a third marking that may be the number "3," to indicate usage of only the first, fourth, and seventh osteotomes in the third mode of use in implant socket formation. Each of the second, the fifth, and the seventh osteotomes may also have a fourth marking that may be the number "4," to indicate usage of only the second, fifth, and seventh osteotomes in the fourth mode of use in implant socket formation.

These marking may quickly enable the dental implant surgeon to identify the osteotomes that may be used for a desired escalation scheme for a particular patient.

It is noted that for this embodiment the first osteotome of the set is referred to as the Tool "0" osteotome merely for convenience, because in another embodiment of the present invention directed to an angulated set, discussed hereinafter, the complete set of six angulated osteotomes may include the same tips as the second through seventh osteotomes of the straight set described above (i.e., the tips of osteotomes "1" through "6").

BRIEF DESCRIPTION OF THE DRAWINGS

The description of the various example embodiments is explained in conjunction with appended drawings, in which.

DETAILED DESCRIPTION OF THE INVENTION

Figure 1:
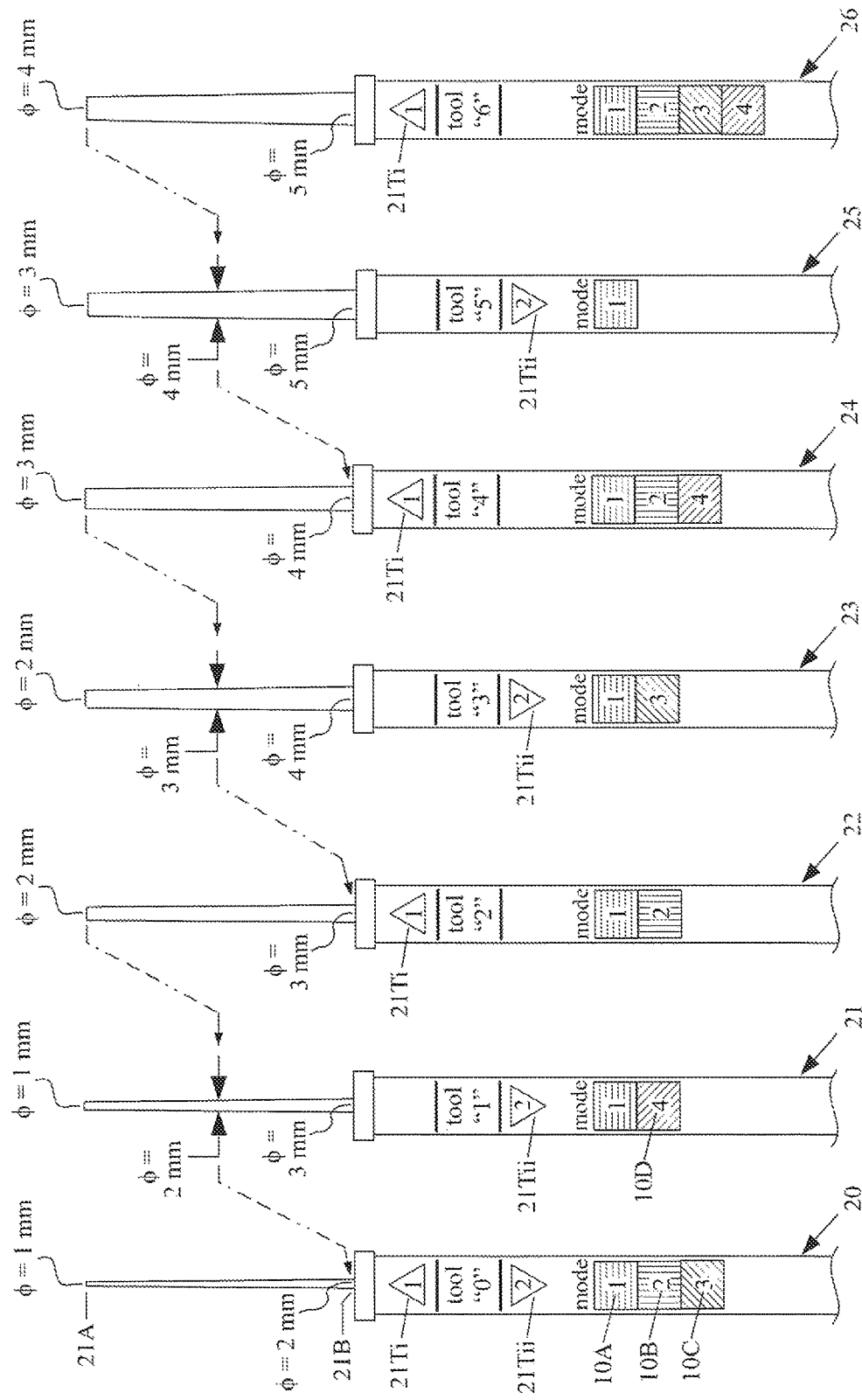
FIG. 1 illustrates a set of straight osteotomes formed in accordance with a first embodiment of the present invention, all of which are usable in a first mode of implant socket formation.

As used throughout this specification, the word "may" is used in a permissive sense (i.e., meaning having the potential to), rather than the mandatory sense (i.e., meaning must). Similarly, the words "include", "including", and "includes" mean including but not limited to.

The phrases "at least one", "one or more", and "and/or" are open-ended expressions that are both conjunctive and disjunctive in operation. For example, each of the expressions "at least one of A, B and C", "one or more of A, B, and C", and "A, B, and/or C" mean all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference.

Furthermore, the described features, advantages, and characteristics of any particular embodiment disclosed herein, may be combined in any suitable manner with any of the other embodiments disclosed herein.

Any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from numeric variation resulting from a stack up (i.e., the sum) of multiple individual tolerances.

It is further noted that any use herein of relative terms such as "top," "bottom," "upper," "lower," "vertical," and "horizontal" are merely intended to be descriptive for the reader, based on the depiction of those features within the figures for one particular position of the device, and such terms are not intended to limit the orientation with which the device of the present invention may be utilized.

Many if not most dental implant surgeons utilize a set of osteotomes, each osteotome of which has a conical tip, with apex and base diameters that increase for successive osteotomes according to the formula devised by R. B. Summers, where the diameter at the apex of a successively larger osteotome is the same as the largest penetrating (e.g. base) diameter of the previous osteotome used.

However, there are problems associated with traditional Summers' type osteotome sets, and their associated tapers. The Summers' diameter escalation scheme essentially applies a constant linear dilation to the bony osteotomy (i.e., the implant socket) whereby the initial diameter of a successively larger osteotome is the same as the largest penetrating diameter of the previous conical osteotome used. However, the residual bony ridge is typically thin at the crest, and widens in the apical direction, i.e., the bone ridge becomes wider and wider in the apical direction, and is therefore less conducive to flexing. Therefore, the Summers' diameter escalation consistently applies this linear force too aggressively at the thin crestal portion of the residual ridge. This excessive force applied to the thin, vulnerable crestal portion often leads to its fracture.

The variable geometry osteotome (VGO) sets disclosed herein utilize a different diameter escalation scheme, which makes the entire process of expanding thin ridges safer, as it does not attempt to hinge the bony walls too fast and too close to the crest, as with the Summer's osteotomes. The variable geometry osteotome (VGO) sets disclosed herein instead first make the deeper bone more conducive to flexing prior to trying to dilate the thin crest. The VGO sets disclosed herein also provide flexibility of use in the form of four different possible modes of use, giving the surgeon more escalation options that may be appropriate for different bone conditions/densities encountered for different osteotomy patients.

The VGO sets disclosed herein use a dual stepwise escalation for the diameters of both tip apices and tip bases, instead of the Summers-type of linear escalation, and which is different from the escalation of Applicants U.S. Pat. No. 9,333,058. This dual stepwise escalation results in less stress on the thin crestal bone, as each of the VGO tips work in succession, such that one tip first prepares the bony hole for what the next tip will do. The VGO tips alternately work on the deeper bony portion first and thereby moves the hinge axis into deeper bone, and then attempts to spread the thinner, weaker crestal bone. By doing work deeper inside the implant socket first, the bony walls are made thinner and therefore more conducive to flexing when the next tool is introduced into hole. This imposes less stress on the thin crest, and makes the expansion process much safer and more predictable.

A first embodiment of straight osteotomes in accordance with the present invention is shown in FIG. 1, and may include osteotomes 20, 21, 22, 23, 24, 25 and 26. Each straight-type osteotome of the set may have a conical working tip with a free end (apex) having a diameter $\phi_{An}$, and a working base having a diameter $\phi_{Bn}$, where the second diameter is larger than the first diameter, $\phi_{Bn} > \phi_{An}$ for each osteotome of the set to provide the conical shape. The first osteotome, n=1, of the set may have the working tip formed with a first diameter, $\phi_{A1}$ at the free end, and a second diameter, $\phi_{B1}$ at the working base. The diameter at the free end alternately increases by a constant increment, k, as a step function, for each successive osteotome of the set beginning with the first osteotome; and the diameter at the working base alternately increases by a constant increment, C, as a step function, beginning with a second osteotome of the set. For an embodiment where the set includes seven osteotomes, as other numbers of osteotomes may similarly be used, the dual stepped diameter escalation may be as shown in the following chart:

| MODE #1 | | |
|---|---|---|
| Osteotome Tool Number | Diameter Tip Apex (mm) | Diameter Tip Base (mm) |
| 0 | 1 | 2 |
| 1 | 1 | 3 |
| 2 | 2 | 3 |
| 3 | 2 | 4 |
| 4 | 3 | 4 |
| 5 | 3 | 5 |
| 6 | 4 | 5 |

Figure 13:
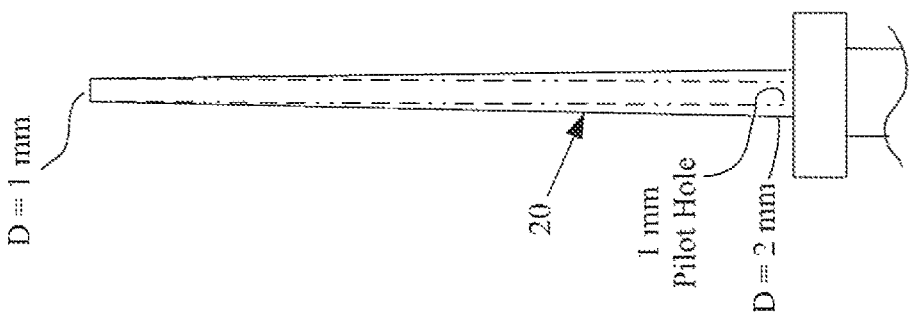
FIG. 13; shows the conical tip portion of the first osteotome in FIG. 1, overlaid upon a pilot hole which it is to enter and enlarge.

In a first mode of use, each of the seven osteotomes may be successively worked into the implant socket for a very gradual escalation sequence. For the first osteotome 20, identified as "tool '0,'" the apex diameter may be 1 mm, and the diameter at the working base may be 2 mm. A pilot hole on the order of 1 mm may be used to begin the implant socket. As shown in FIG. 13, both the apex and base diameters of osteotome 20 will be working to widen the socket, as well as the entire conically-shaped surface in between those end diameters. This may be indicated by a symbol formed on the osteotome. In one embodiment a triangle symbol 21Ti may be used, and which may point to towards the tip when the tip is active, and a second triangle symbol 21Tii may be used when the base is active, which second triangle may point away from the tip. In the case of the first osteotome 20 (tool "0"), since both the apex and base diameters may be working to enlarge the socket for such a pilot hole size, it may have both triangle symbols 21Ti and 21Tii formed thereon. The triangle may have a "1" inscribed therein when pointing toward the tip (i.e., for triangle 21Ti), and may have a "2" inscribed therein when pointing away from the tip (i.e., for triangle 21Tii). The respective triangle symbols 21Ti and 21Tii may also be positioned on opposite sides of the tool label (i.e., above and below "tool '0'"), as shown in FIG. 1, to further correspond to the distal ends of the conical tip.

It is noted that a difference between the apex diameter and the base diameter for each of the six osteotomes 21/22/23/24/25/26 of set 10 (i.e., other than osteotome 20, Tool "0") is either 1 or 2, and these delta values may be respectively marked on the osteotome within the triangle symbol 21Ti and triangle symbol 21Tii may serve to immediately inform the dental implant surgeon as to the nature of each particular tip, namely which part of tip (apex or base) is the active part, and which part of tip is the passive part for that particular tool. For each of the osteotome tools (i.e., 32, 34, and 36)

that have a delta of "1" (and are labeled with triangle symbol 21Ti), the tip is fully active at the apex, with such activity for widening the implant socket gradually decreasing (becomes less active) with increasing proximity to the base dimeter of the tip, and the base of the tool is completely inactive. For each of the osteotome tools (i.e., 33, and 35) that have a delta of "2" (and are labeled with triangle symbol 21Tii), the tip is fully active at the base, with such activity for widening the implant socket gradually decreasing (becomes less active) with increasing proximity to the apex dimeter of the tip, and the apex of the tool is completely inactive. Therefore, the tools with a delta of "1" may require less caution when used, since they are not dilating the thin crestal portion of the osteotomy, and instead are dilating the deeper, wider, and stronger portion of the osteotomy. Similarly, tools with a delta of "2" may require more caution when used, since these tools are dilating the weaker and thinner portion of the bone, namely the thin Crestal area. Therefore, in one embodiment the delta values of "1" or "2" are marked on instrument handles (e.g., within triangle symbol 21Ti and/or triangle symbol 21Tii) to add value to the kit, by providing this information to the surgeon, which may eliminate the need for the implant surgeon to calculate a delta value for the tool manually or in his/her head. These and any other markings that may be utilized herein can be added onto the osteotomes using any methods known in the art, including, but not limited to, laser etching, printing, placards, etc.

In another embodiment, rather than a triangles the symbol may instead be a circle that may be colored green to indicate that the apex of the tip is active, and may be a circle that is colored yellow or red when indicate that the base of the tip is active, with those yellow and red colors indicating caution, so that diligence may be used to be alert to excessive pressure at the crest that might cause it to split.

Figure 14:
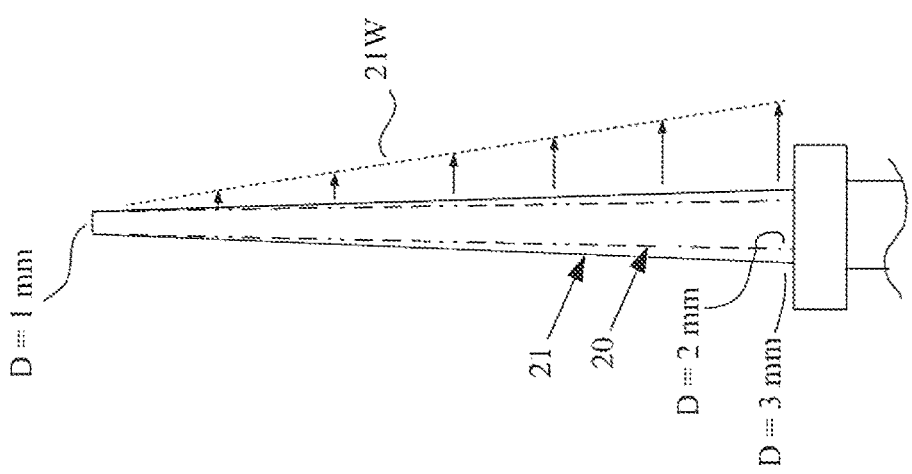
FIG. 14 shows the conical tip portion of the second osteotome in FIG. 1 overlaid on the conical tip portion of the first osteotome shown therein.

After the first osteotome 20 has been used to widen the implant socket and the second osteotome 21 is inserted into the opening, its 1 mm apex diameter will not be doing any widening, as it has the same size apex diameter as osteotome 20. The lower portion of the conically-shaped tip of osteotome 21 proximate to the base will be doing most of the widening, which is indicated by the triangle 21Tii. This may be understood from FIG. 14, which shows the conical tip portion of the second osteotome 21 overlaid on the conical tip portion of the first osteotome 20, and highlights the difference in tapers with the increasingly larger laterally-oriented arrows near the base, all of which terminate on line 21W. Moreover, the widening accomplished by osteotome 21 may only begin to occur when roughly one-half of the tip of osteotome 21 is inserted into the socket, as the diameter at its mid-point is roughly 2 mm for the straight linear taper between 1 mm and 3 mm (see FIG. 1), which should be roughly the socket opening diameter formed by the previous osteotome. This is indicated by the dotted/dashed arrow pointing from the 2 mm diameter at the mid-point of osteotome 21 to the 2 mm diameter at the base of osteotome 20 in FIG. 1.

Figure 15:
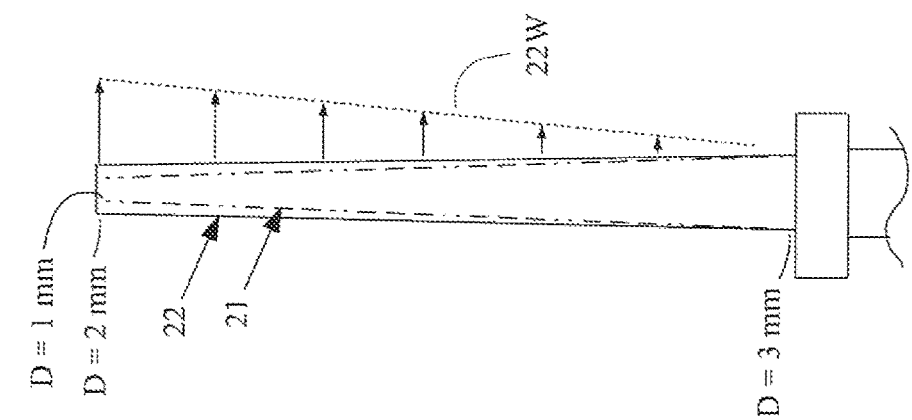
FIG. 15 shows the conical tip portion of the third osteotome in FIG. 1 overlaid on the conical tip portion of the second osteotome shown therein.

Ater the second osteotome 21 has been used to widen the implant socket and the third osteotome 22 is inserted into the opening, its 3 mm base diameter will not be doing any widening, as it has the same size base diameter as osteotome 21. The upper portion of the conically-shaped tip of osteotome 22 proximate to the apex will be doing most of the widening, which is indicated by the triangle 21Ti. This may be understood from FIG. 15, which shows the conical tip portion of the third osteotome 22 overlaid on the conical tip portion of the second osteotome 21, and highlights the difference in tapers with the increasingly larger laterally-oriented arrows near the apex, all of which terminate on line 22W in FIG. 15. Similarly, the widening accomplished by the third osteotome 22 may only begin to occur when roughly one-half of the tip of osteotome 22 is inserted into the socket, where the 2 mm diameter at its apex should contact the 2 mm diameter socket opening formed by the previous osteotome. This is indicated in FIG. 1 by the dotted/dashed arrow pointing from the 2 mm diameter at the apex of osteotome 22 to the 2 mm diameter at roughly the midpoint of osteotome 21.

Osteotomes 23 and 24 have similar relationships and use with respect to each other and to osteotome 22 and the socket formed by it, as is illustrated above for osteotomes 21 and 22 with respect to osteotome 20 and the socket formed by their use.

Also, osteotomes 25 and 26 have similar relationships and use with respect to each other and to osteotome 24 and the socket formed by it, as illustrated above for osteotomes 21 and 22 with respect to osteotome 20 and the socket formed by their use.

Figure 2:
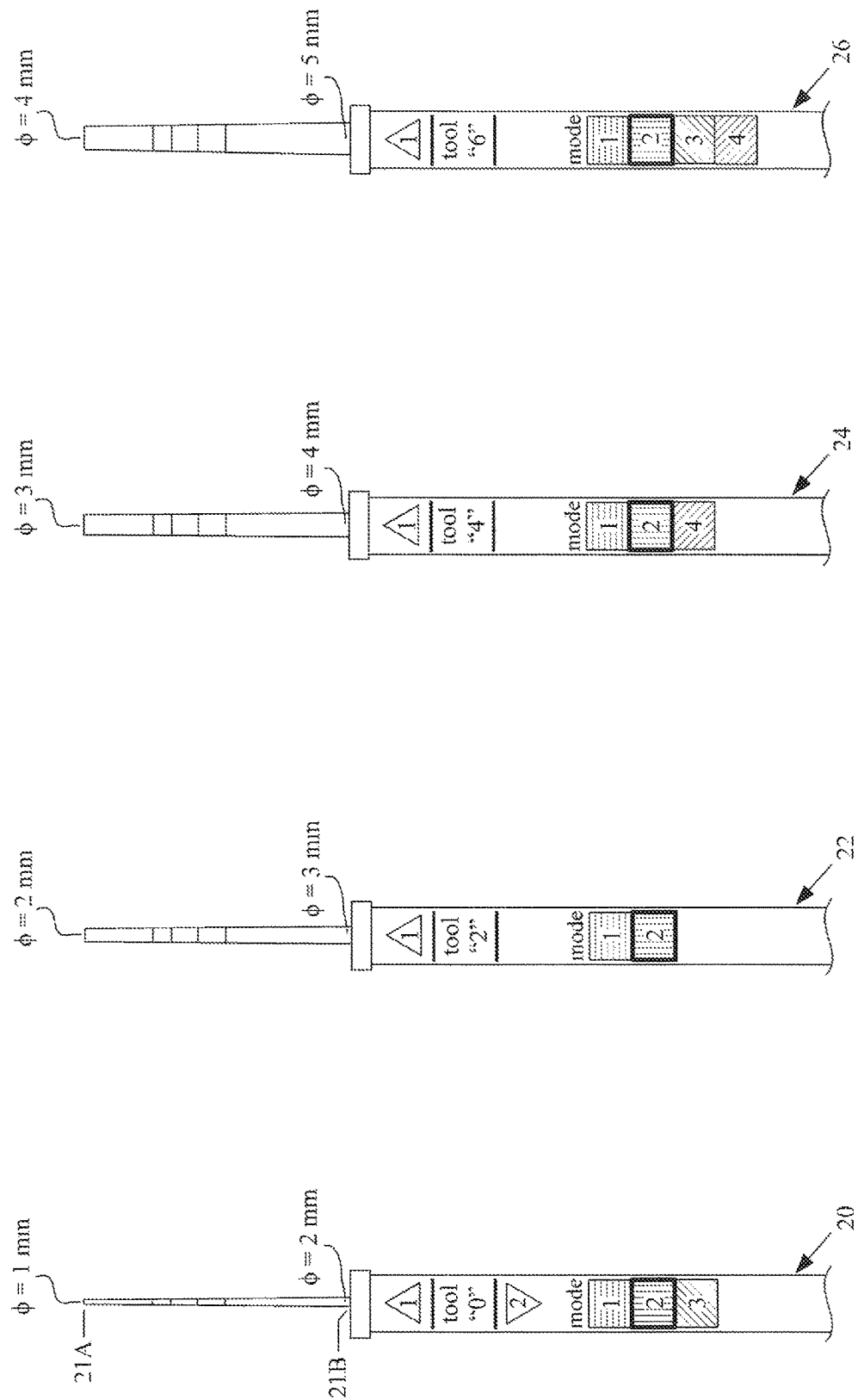
FIG. 2 illustrates a first portion of the straight osteotomes of FIG. 1, being the first, third, fifth, and seventh osteotomes of the set, which four osteotomes are usable in a second mode of implant socket formation.
Figure 3:
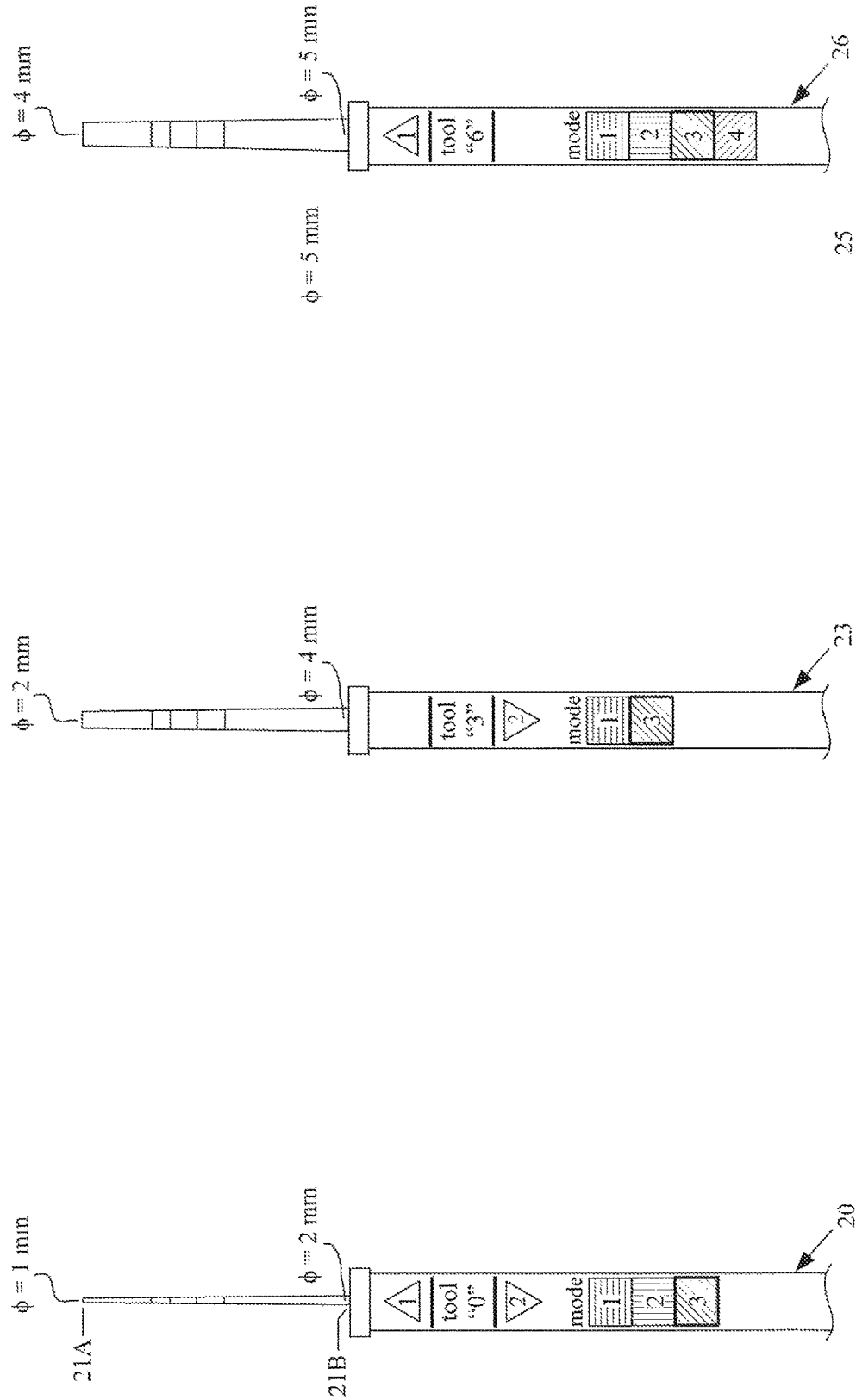
FIG. 3 illustrates a second portion of the straight osteotomes of FIG. 1, being the first, fourth, and seventh osteotomes of the set, which three osteotomes are usable in a third mode of implant socket formation.
Figure 4:
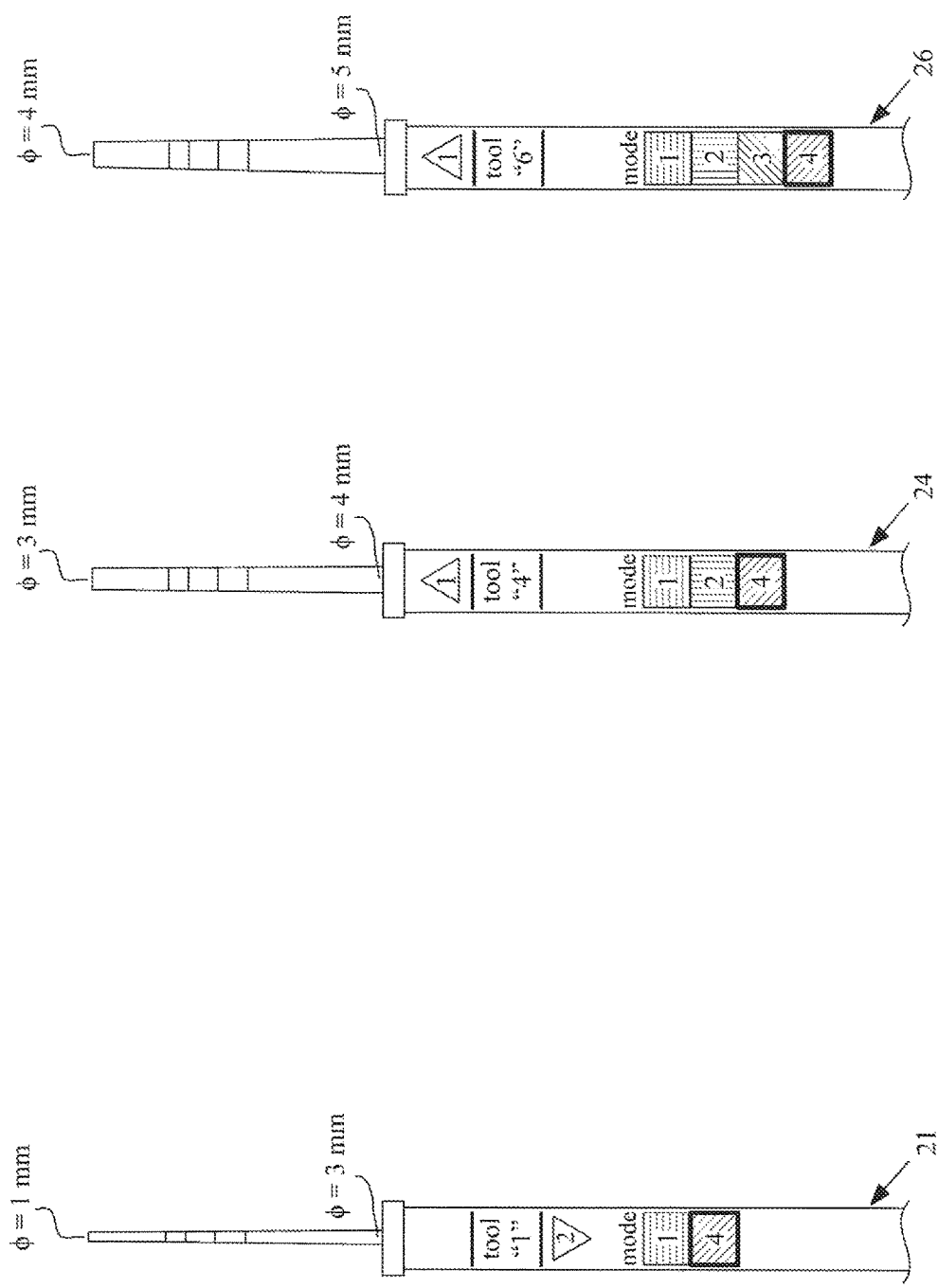
FIG. 4 illustrates a third portion of the straight osteotomes of FIG. 1, being the second, fifth, and seventh osteotomes of the set, which three osteotomes are usable in a fourth mode of implant socket formation.

In a second mode of use for the osteotome set 10, which is illustrated in FIG. 2, only the first osteotome 20 (tool "0"), the third osteotome 22 (tool "2"), the fifth osteotome 24 (tool "4"), and the seventh osteotome 26 (Tool "6") are successively worked into the implant socket for a typical Summers diameter escalation. In an embodiment that may have nine osteotomes in the set, an additional osteotome may serve to widen the implant socket beyond the 5 mm diameter of the base of osteotome 26 shown in FIG. 2.

In a third mode of use, only the first osteotome 20 (Tool "0"), the fourth osteotome 23 (Tool "3"), and the seventh osteotome 26 (Tool "6") are successively worked into the implant socket for a more aggressive Summers diameter escalation—being more aggressive in that the escalation to the same highest diameter occurs using fewer steps/osteotomes.

In a fourth mode of use, only the second osteotome 21 (Tool "1"), the fifth osteotome 24 (Tool "4"), and the seventh osteotome 26 (Tool "6") are successively worked into the implant socket for an even more aggressive Summers' diameter escalation—being more aggressive in that the escalation to the highest diameter occurs using larger diameter sizes.

To inform the dental implant surgeon of these modes of use, each of the osteotomes 20/21/22/23/24/25/26 of set 10 may include a first particular marking 10A that may be the number "1," to indicate usage of each of the seven osteotomes in the first mode of use for implant socket formation. Each of the first osteotome 20, the third osteotome 22, the fifth osteotome 24, and the seventh osteotome 26 may also have a second particular marking 10B thereon that may be the number "2." to indicate usage of only the first, third, fifth, and seventh osteotomes in the second mode of use for implant socket formation. Each of the first osteotome 20, the fourth osteotome 23, and the seventh osteotome 26 may also have a third particular marking 10C that may be the number "3," to indicate usage of only the first, fourth, and seventh osteotomes in the third mode of use for implant socket formation. Each of the second osteotome 21, the fifth osteotome 24, and the seventh osteotome 26 may also have a fourth marking 10D that may be the number "4," to indicate usage of only the second, fifth, and seventh osteotomes in the fourth mode of use for implant socket formation.

These markings 10A, 10B, 10C, and 10D may quickly enable the dental implant surgeon to identify the osteotomes that may be used for a desired escalation scheme for a particular patient. Each of those markings 10A, 10B, 10C, and 10D may be positioned upon a respectively different background, such as the varied hatching shown in FIG. 1. The different backgrounds may also be different colors.

Each of the straight osteotomes 20, 21, 22, 23, 24, 25, and 26 of set 10 may have depth markings at 8 mm, 10 mm, 13 mm, and 16 mm, as shown on the osteotomes of FIG. 2.

It is noted that for this embodiment the first osteotome 20 of the set 10 is referred to as the Tool "0" osteotome merely for convenience, because in another embodiment of the present invention directed to an angulated set, discussed hereinafter, the set of six angulated osteotomes may include the same tips as the second through seventh osteotomes of the straight set described above (i.e., the tips of Tools "1" through "6"). Tool "0" is unique and introduced only in the straight VGO set 10 of osteotomes, having an apical diameter of 1.0 mm and a base diameter of 2.0 mm, as it is intended to be used in the anterior portion of the mouth where thinner residual ridges are often encountered. Therefore, a narrower tool is used to address this fact, and to deal with the thinner bony ridges often found in the Pre-maxilla.

Figure 5:
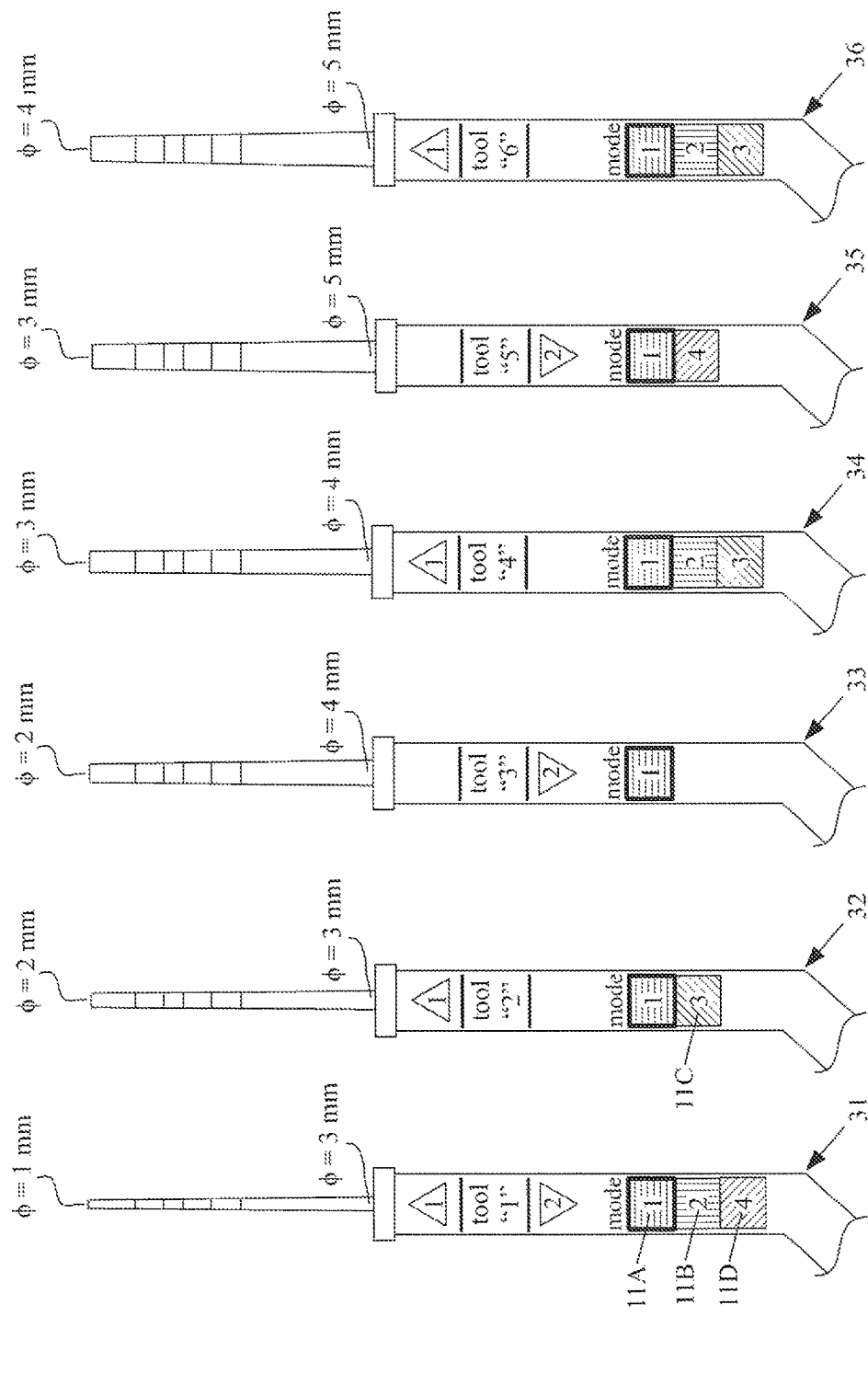
FIG. 5 illustrates a set of angulated osteotomes formed in accordance with another embodiment of the present invention, all of which are usable in a first mode of implant socket formation.

A first set of angulated osteotomes 11 is shown in FIG. 5, and may include osteotomes 31, 32, 33, 34, 35, and 36, each of which may have depth markings at 8 mm, 10 mm, 13 mm, and 16 mm. The tips of osteotomes 31, 32, 33, 34, 35, and 36 of set 11 may be formed the same as the tips of osteotomes 21, 22, 23, 24, 25, and 26 of set 10, and may be similarly used. Each of osteotomes 31, 32, 33, 34, 35, and 36 may be used in a first mode of use for implant socket formation, and may have first particular marking 11A that may be the number "1" to indicate such usage.

Figure 6:
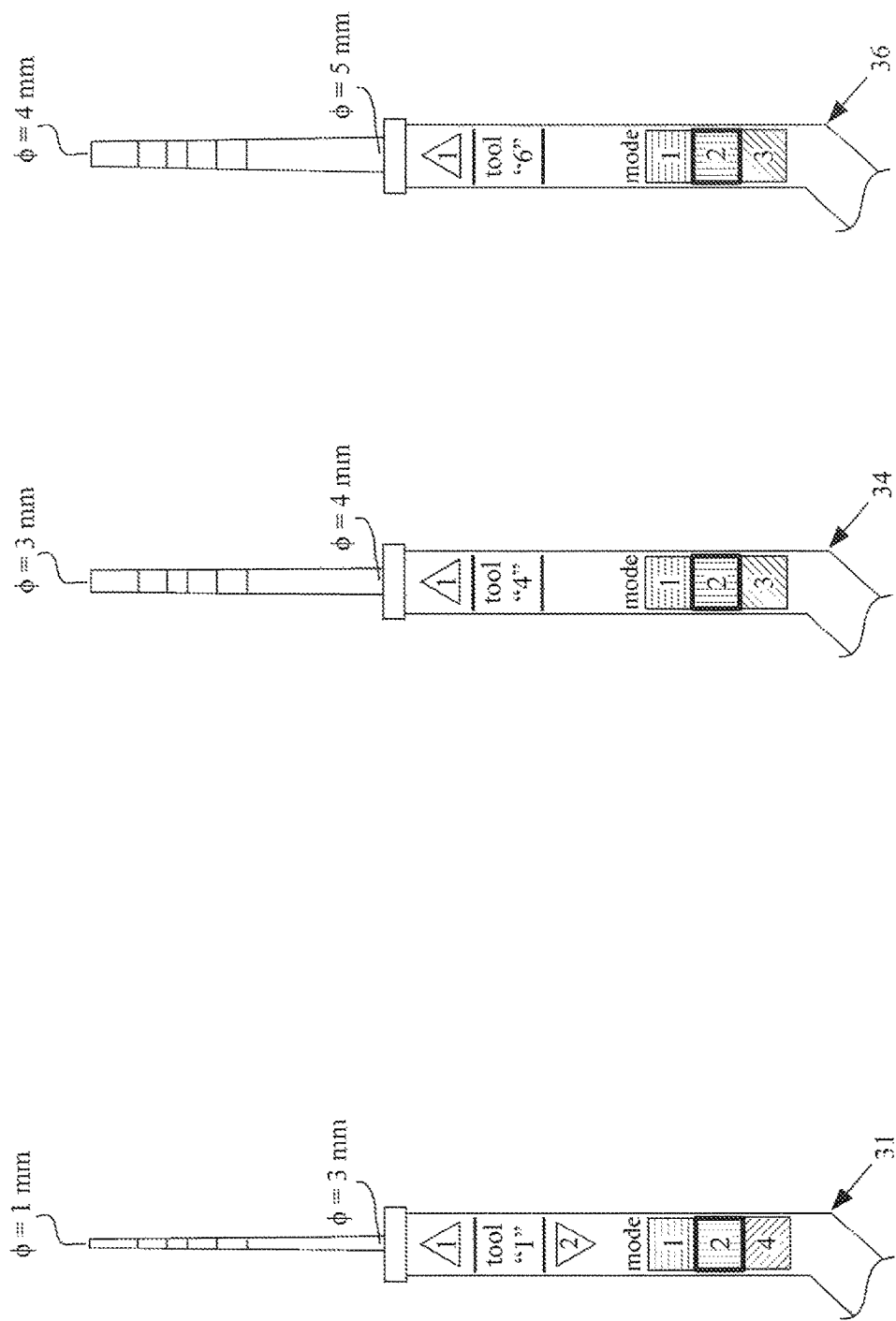
FIG. 6 illustrates a first portion of the angulated osteotomes of FIG. 5, being the first, fourth, and sixth osteotomes of that set, which three osteotomes are usable in a second mode of implant socket formation.

In a second mode of use of the angulated osteotome set 11, which is illustrated in FIG. 6, only the osteotome 31 (tool "1"), the osteotome 34 (tool "4"), and the osteotome 36 (Tool "6") are successively worked into the implant socket for a typical Summers' diameter escalation.

Figure 7:
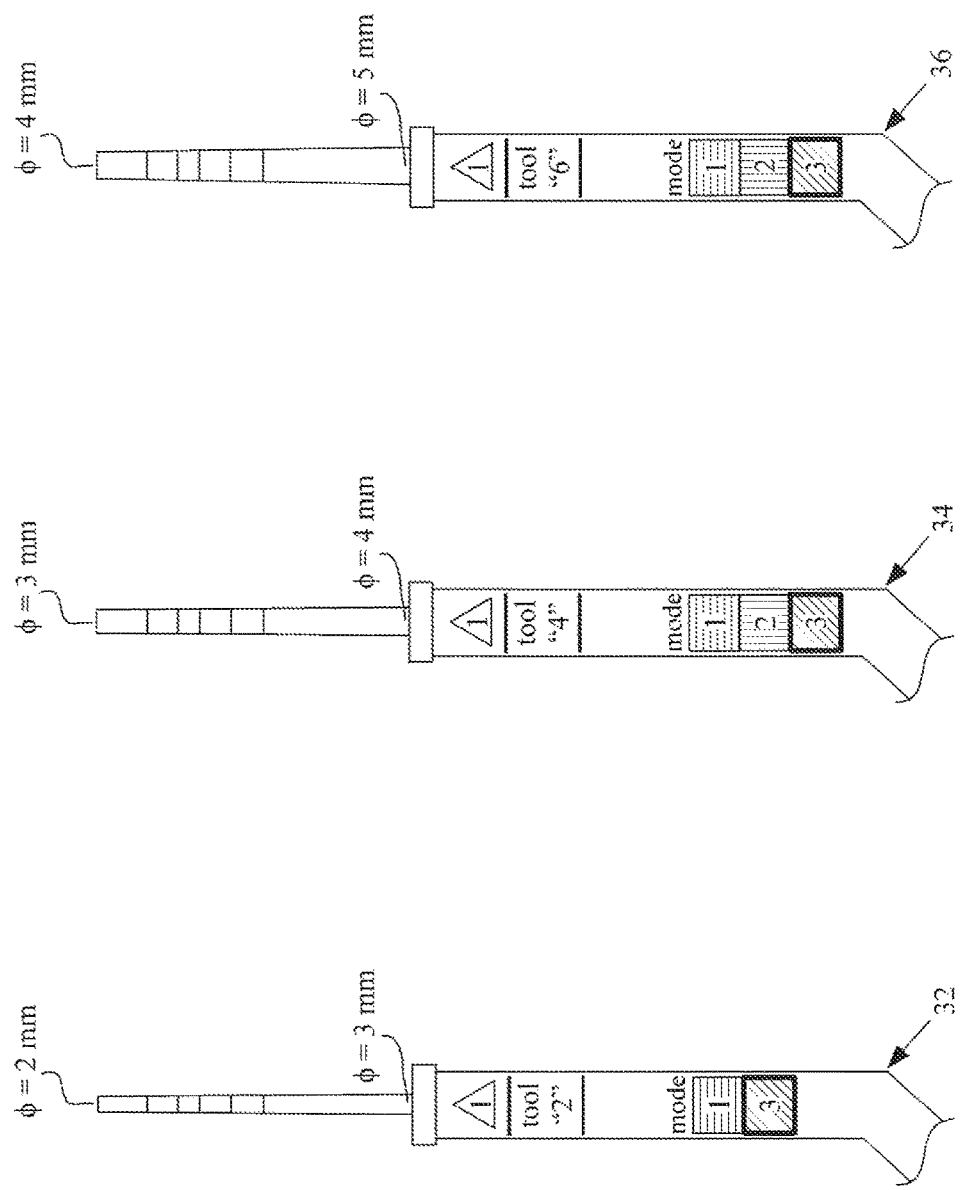
FIG. 7 illustrates a second portion of the angulated osteotomes of FIG. 5, being the second, fourth, and sixth osteotomes of that set, which three osteotomes are usable in a third mode of implant socket formation.

In a third mode of use of the angulated osteotome set 11, which is illustrated in FIG. 7, only osteotome 32 (Tool "2"), the osteotome 34 (Tool "4"), and the 36 osteotome (Tool "6") are successively worked into the implant socket for a more aggressive Summers diameter escalation-being more aggressive in that the escalation begins with a higher initial diameter.

Figure 8:
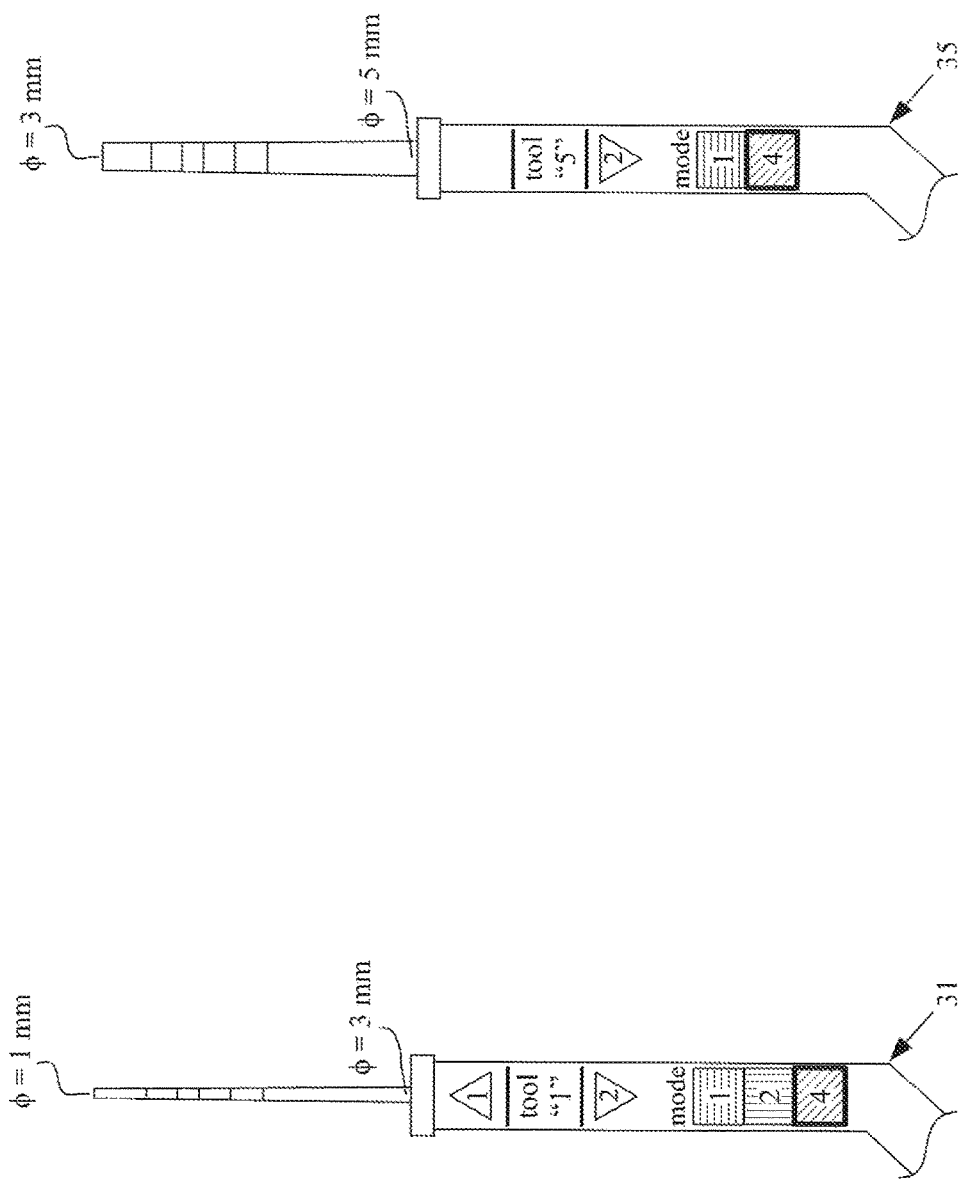
FIG. 8 illustrates a third portion of the angulated osteotomes of FIG. 5, being the first, and fifth osteotomes of that set, which two osteotomes are usable in a fourth mode of implant socket formation.

In a fourth mode of use of the angulated osteotome set 11, which is illustrated in FIG. 8, only the osteotome 31 (Tool "1"), and the osteotome 36 (Tool "6") are successively worked into the implant socket for an even more aggressive Summers' diameter escalation—being more aggressive in that the escalation to the highest diameter occurs using larger diameter sizes.

To inform the dental implant surgeon of these modes of use, each of the osteotomes 31, 32, 33, 34, 35, and 36 of set 11 may include a first particular marking 11A that may be the number "1," to indicate usage of each of the six osteotomes in the first mode of use for implant socket formation. Each of osteotome 31, osteotome 34, and osteotome 36 may also have a second particular marking 11B thereon that may be the number "2," to indicate usage of only those osteotomes in the second mode of use for implant socket formation. Each of osteotome 32, osteotome 34, and osteotome 36 may also have a third particular marking 11C that may be the number "3," to indicate usage of only those osteotomes in the third mode of use for implant socket formation. Each of osteotome 31, and the osteotome 35 may also have a fourth marking 11D that may be the number "4," to indicate usage of only the second, fifth, and seventh osteotomes in the fourth mode of use for implant socket formation.

Figure 9:
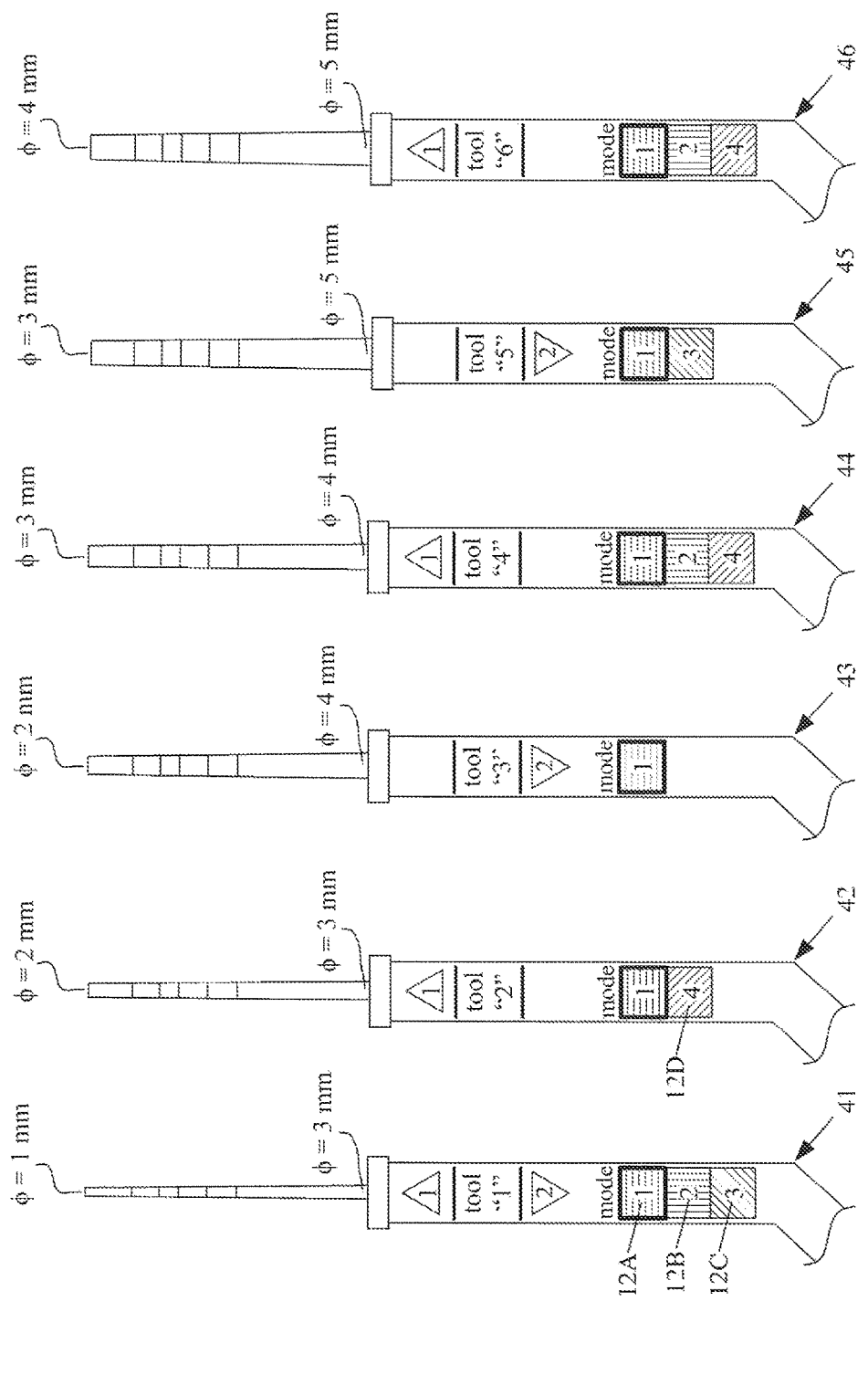
FIG. 9 illustrates a set of angulated osteotomes formed in accordance with yet another embodiment of the present invention, all of which are usable in a first mode of implant socket formation.

A second set of angulated osteotomes 12 is shown in FIG. 9, and may include osteotomes 41, 42, 43, 44, 45, and 46, which may be formed the same as osteotomes 31, 32, 33, 34, 35, and 36 of set 11, except that they may have different markings to identify different modes of use, as follows.

Each of osteotomes 41, 42, 43, 44, 45, and 46 may be used in a first mode of use for implant socket formation, and may have first particular marking 12A that may be the number "1" to indicate such usage.

Figure 10:
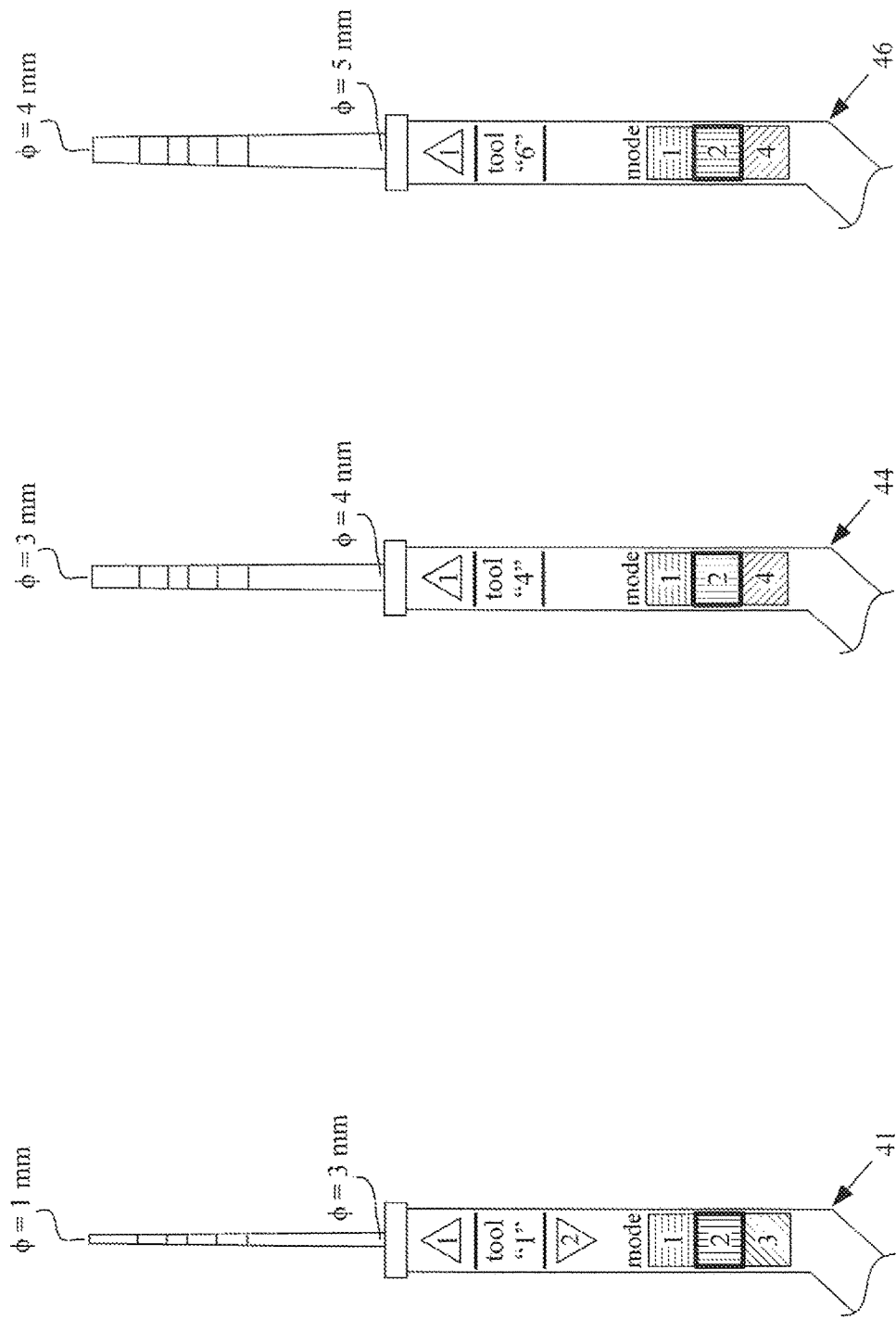
FIG. 10 illustrates a first portion of the angulated osteotomes of FIG. 9, being the first, fourth, and sixth osteotomes of that set, which three osteotomes are usable in a second mode of implant socket formation.

In a second mode of use, which is illustrated in FIG. 10, only osteotome 41 (tool "1"), osteotome 44 (tool "4"), and osteotome 46 (Tool "6") are successively worked into the implant socket for a typical Summers' diameter escalation, and each of those osteotomes may have a second particular marking 12B that may be the number "2" to indicate such usage.

Figure 11:
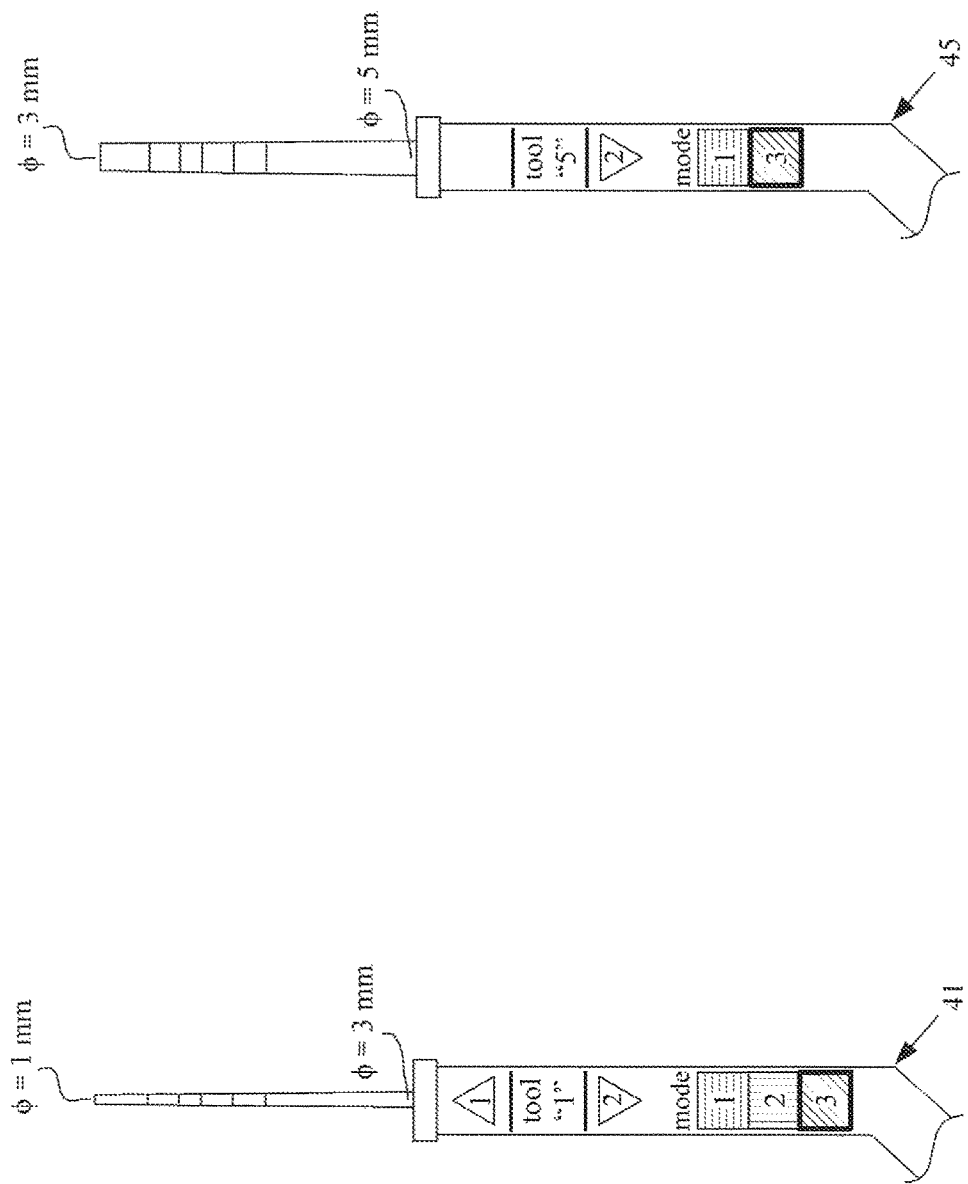
FIG. 11 illustrates a second portion of the angulated osteotomes of FIG. 9, being the first, and fifth osteotomes of that set, which two osteotomes are usable in a third mode of implant socket formation.

In a third mode of use illustrated in FIG. 11, only osteotome 41 (Tool "1"), and osteotome 45 (Tool "5") are successively worked into the implant socket for an aggressive Summers diameter escalation, and each of those osteotomes may have a third particular marking 12C that may be the number "3" to indicate such usage.

Figure 12:
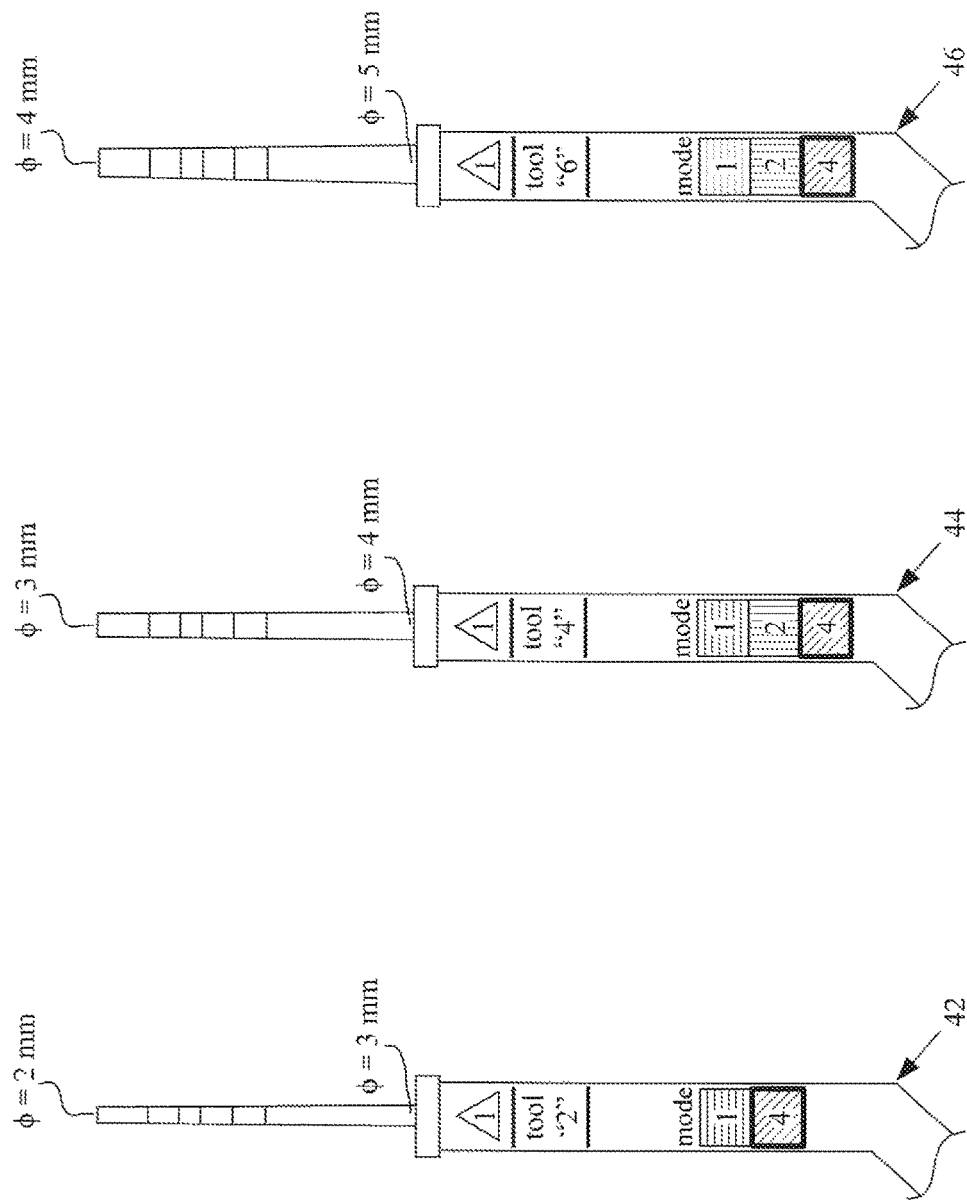
FIG. 12 illustrates a third portion of the angulated osteotomes of FIG. 11, being the first, and fifth osteotomes of that set, which two osteotomes are usable in a fourth mode of implant socket formation.

In a fourth mode of use illustrated in FIG. 12, only the osteotome 31 (Tool "1"), and the osteotome 36 (Tool "6") are successively worked into the implant socket for an even more aggressive Summers' diameter escalation, and each of those osteotomes may have a fourth particular marking 12D that may be the number "4" to indicate such usage.

While illustrative implementations of one or more embodiments of the present invention are provided hereinabove, those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A set of straight osteotomes, for use during implant socket formation of an osteotomy to reduce crestal alveolar stress and likelihood of a crestal fracture, each said osteotome of said set comprising a conical working tip with a free end having a diameter $\phi_{An}$, and a working base having a diameter $\phi_{Bn}$; a first osteotome, n=1, of said set comprising said working tip formed with a first diameter, $\phi_{A1}$ at said free end, and with a second diameter, $\phi_{B1}$ at said working base, said second diameter being larger than said first diameter, $\phi_{Bn} > \phi_{An}$ for each osteotome of said set; and wherein said diameter at said free end alternately increases by a constant increment, k, as a step function, for each successive osteotome of said set beginning with said first osteotome; and wherein said diameter at said working base alternately increases by a constant increment, C, as a step function, beginning with a second osteotome of said set.

2. The set of straight osteotomes according to claim 1,
wherein said first osteotome has a diameter $\phi_{A1}$ of about 1 mm at said free end, and a diameter $\phi_{B1}$ of about 2 mm at said working base;
wherein said second osteotome has a diameter $\phi_{A2}$ of about 1 mm at said free end, and a diameter, $\phi_{B2}$ of about 3 mm at said working base;

wherein said set comprises a third osteotome with a diameter $\phi_{A3}$ of about 2 mm at said free end, and a diameter, $\phi_{B3}$ of about 3 mm at said working base;

wherein said set comprises a fourth osteotome with a diameter $\phi_{A4}$ of about 2 mm at said free end, and a diameter, $\phi_{B4}$ of about 4 mm at said working base;

wherein said set comprises a fifth osteotome with a diameter $\phi_{A5}$ of about 3 mm at said free end, and a diameter, $\phi_{B5}$ as of about 4 mm at said working base;

wherein said set comprises a sixth osteotome with a diameter $\phi_{A6}$ of about 3 mm at said free end, and a diameter, $\phi_{B6}$ of about 5 mm at said working base; and wherein said set comprises a seventh osteotome with a diameter $\phi_{A7}$ of about 4 mm at said free end, and a diameter, $\phi_{B7}$ of about 5 mm at said working base.

3. The set of straight osteotomes according to claim 2,
wherein each of said seven osteotomes comprises a first marking comprising the number 1, to indicate usage of each of said seven osteotomes in a first mode of implant socket formation; and wherein said first, said third, said fifth, and said seventh osteotomes each comprises a second marking comprising the number 2, to indicate usage of only said first, third, fifth, and seventh osteotomes in a second mode of implant socket formation.

4. The set of straight osteotomes according to claim 3,
wherein said first, said fourth, and said seventh osteotomes each comprise a third marking comprising the number 3, to indicate usage of only said first, fourth, and seventh osteotomes in a third mode of implant socket formation; and wherein said second, said fifth, and said seventh osteotomes each comprise a fourth marking comprising the number 4, to indicate usage of only said second, fifth, and seventh osteotomes in a fourth mode of implant socket formation.

5. The set of straight osteotomes according to claim 4, further comprising:
a fifth marking on each of said first, third, fifth, and seventh osteotomes, said fifth marking configured to point toward said tip to indicate said free end of each said osteotome tip being active during the implant socket formation; and a sixth marking on each of said second, fourth, and sixth osteotomes, said sixth marking configured to point away said tip to indicate said base of each said osteotome tip being active during the implant socket formation.

6. The set of straight osteotomes according to claim 5,
wherein each said first marking is formed upon a first background;

wherein each said second marking is formed upon a second background;

wherein each said third marking is formed upon a third background; and wherein each said first fourth marking is formed upon a fourth background.

7. The set of straight osteotomes according to claim 1, wherein each said osteotome comprises four graduated depth lines on said tip at respective distances of 8 mm, 10 mm, 13 mm, and 16 mm from said free end.

8. A set of angulated osteotomes, for use during implant socket formation of an osteotomy to reduce crestal alveolar stress and likelihood of a crestal fracture, each said osteotome of said set comprising a conical working tip with a free end having a diameter an, and a working base having a diameter $\phi_{Bn}$; a first osteotome, n=1, of said set comprising said working tip formed with a first diameter, $\phi_{A1}$ at said free end, and with a second diameter, $\phi_{B1}$ said working base, said second diameter being larger than said first diameter, $\phi_{Bn}>\phi_{An}$, each osteotome of said set; and wherein said diameter at said free end alternately increases by a constant increment, k, as a step function, for each successive osteotome of said set beginning with a second osteotome; and wherein said diameter at said working base alternately increases by a constant increment, C, as a step function, beginning with said first osteotome.

9. The set of angulated osteotomes according to claim 8,
wherein said first osteotome has a diameter $\phi_{A1}$ of about 1 mm at said free end, and a diameter $\phi_{B1}$ of about 3 mm at said working base;

wherein said set comprises a second osteotome with a diameter $\phi_{A2}$ of about 2 mm at said free end, and a diameter, $\phi_{B2}$ of about 3 mm at said working base;

wherein said set comprises a third osteotome with a diameter $\phi_{A3}$ of about 2 mm at said free end, and a diameter, $\phi_{B3}$ of about 4 mm at said working base;

wherein said set comprises a fourth osteotome with a diameter $\phi_{A4}$ of about 3 mm at said free end, and a diameter, $\phi_{B4}$ of about 4 mm at said working base;

wherein said set comprises a fifth osteotome with a diameter $\phi_{A5}$ of about 3 mm at said free end, and a diameter, $\phi_{B5}$ of about 5 mm at said working base; and wherein said set comprises a sixth osteotome with a diameter $\phi_{A6}$ of about 4 mm at said free end, and a diameter, $\phi_{B6}$ of about 5 mm at said working base.

10. The set of angulated osteotomes according to claim 9,
wherein each of said six osteotomes comprises a first marking comprising the number 1, to indicate usage of each of said six osteotomes in a first mode of implant socket formation; and wherein said first, said fourth, and said sixth osteotomes each comprises a second marking comprising the number 2, to indicate usage of only said first, fourth, and sixth osteotomes in a second mode of implant socket formation.

11. The set of angulated osteotomes according to claim 10,
wherein said second, said fourth, and said sixth osteotomes each comprise a third marking comprising the number 3, to indicate usage of only said second, fourth, and sixth osteotomes in a third mode of implant socket formation; and wherein said first, and said fifth osteotomes each comprise a fourth marking comprising the number 4, to indicate usage of only said first, and fifth osteotomes in a fourth mode of implant socket formation.

12. The set of angulated osteotomes according to claim 11, further comprising:
a fifth marking on each of said first, third, fifth, and seventh osteotomes, said fifth marking configured to point toward said tip to indicate said free end of each said osteotome tip being active during the implant socket formation; and a sixth marking on each of said second, fourth, and sixth osteotomes, said sixth marking configured to point away said tip to indicate said base of each said osteotome tip being active during the implant socket formation.

13. The set of angulated osteotomes according to claim 12,
wherein each said first marking is formed upon a first background;

wherein each said second marking is formed upon a second background;

wherein each said third marking is formed upon a third background; and wherein each said first fourth marking is formed upon a fourth background.

14. The set of angulated osteotomes according to claim 13, wherein each said osteotome comprises five graduated depth lines on said tip at respective distances of about 5 mm, about 8 mm, about 10 mm, about 13 mm, and about 16 mm from said free end.

15. A method of performing dental implant socket formation using a set of seven straight osteotomes comprising:

forming a first of said set of seven osteotomes with a diameter of about 1 mm at a free end thereof, and with a diameter of about 2 mm at a working base thereof;

forming a second of said set of seven osteotomes with a diameter of about 1 mm at a free end thereof, and with a diameter of about 3 mm at a working base thereof;

forming a third of said set of seven osteotomes with a diameter of about 2 mm at a free end thereof, and with a diameter of 3 mm at a working base thereof;

forming a fourth of said set of seven osteotomes with a diameter of about 2 mm at a free end thereof, and with a diameter of 4 mm at a working base thereof;

forming a fifth of said set of seven osteotomes with a diameter of about 3 mm at a free end thereof, and with a diameter of about 4 mm at a working base thereof;

forming a sixth of said set of seven osteotomes with a diameter of about 3 mm at a free end thereof and with a diameter of about 5 mm at a working base thereof; and forming a seventh of said set of seven osteotomes with a diameter of about 4 mm at a free end thereof, and a diameter of about 5 mm at a working base thereof;

using each of said first, second, third, fourth, fifth, sixth, and seventh osteotomes successively for a gradual diameter escalation during implant socket formation; and alternatively using only said first, third, fifth, and seventh osteotomes for a conventional summers diameter escalation during implant socket formation.

16. The method according to claim 15, further comprising:

alternatively using only said first, fourth, and seventh osteotomes for an aggressive summers diameter escalation during implant socket formation.

17. The method according to claim 16, further comprising:

alternatively using only said second, fifth, and seventh osteotomes for a more aggressive summers diameter escalation during implant socket formation.

18. A method of performing dental implant socket formation using a set of six angulated osteotomes comprising:

forming a first of said set of six osteotomes with a diameter of about 1 mm at a free end thereof, and with a diameter of about 3 mm at a working base thereof;

forming a second of said six osteotomes with a diameter of about 2 mm at a free end thereof, and with a diameter of about 3 mm at a working base thereof;

forming a third of said six osteotomes with a diameter of about 2 mm at a free end thereof, and with a diameter of about 4 mm at a working base thereof;

forming a fourth of said six osteotomes with a diameter of about 3 mm at a free end thereof, and with a diameter of about 4 mm at a working base thereof;

forming a fifth of said six osteotomes with a diameter of about 3 mm at a free end thereof, and with a diameter of about 5 mm at a working base thereof; and forming a sixth of said set of six osteotomes with a diameter of about 4 mm at a free end thereof, and a diameter of about 5 mm at a working base thereof;

using each of said first, second, third, fourth, fifth, and sixth osteotomes successively for a gradual diameter escalation during implant socket formation; and alternatively using only said first, fourth, and sixth osteotomes for a conventional summers diameter escalation during implant socket formation.

19. The method according to claim 18, further comprising:

alternatively using only said second, fourth, and sixth osteotomes for an aggressive summers diameter escalation during implant socket formation.

20. The method according to claim 19, further comprising:

alternatively using only said first and fifth osteotomes for a more aggressive summers diameter escalation during implant socket formation.

* * * * *